United States Patent
Schmidt et al.

(10) Patent No.: US 6,309,348 B1
(45) Date of Patent: Oct. 30, 2001

(54) ENDOMICROSCOPE SYSTEM

(75) Inventors: Martin Schmidt, Bad Schwartau; Jörg Draeger, Hamburg; Christian Fenske, Lüneburg, all of (DE)

(73) Assignee: Möller-Wedel GmbH, Wedel (DE)

( * ) Notice: Subject to any disclaimer, the term of this patent is extended or adjusted under 35 U.S.C. 154(b) by 0 days.

(21) Appl. No.: 09/452,215

(22) Filed: Dec. 1, 1999

(30) Foreign Application Priority Data

Dec. 2, 1998 (EP) .................................................. 98122900

(51) Int. Cl.⁷ ............................ A61B 1/005; G02B 21/26
(52) U.S. Cl. ........................ 600/162; 600/168; 600/172; 359/391
(58) Field of Search .................................... 600/101, 102, 600/162, 166, 111, 168, 172, 165; 359/377, 378, 381, 391, 393; 385/116, 119

(56) References Cited

U.S. PATENT DOCUMENTS

| | | | |
|---|---|---|---|
| 4,364,629 | * 12/1982 | Lang et al. | 600/166 |
| 5,295,477 | * 3/1994 | Janfaza | 600/166 |
| 5,321,447 | * 6/1994 | Sander et al. | 351/216 |
| 5,419,312 | * 5/1995 | Arenberg et al. | 600/188 |
| 5,496,261 | * 3/1996 | Sander | 600/163 |
| 5,957,832 | * 9/1999 | Taylor et al. | 600/114 |

* cited by examiner

*Primary Examiner*—John P. Leubecker
(74) *Attorney, Agent, or Firm*—Alix, Yale & Ristas, LLP

(57) ABSTRACT

The endomicroscope system includes an operation microscope and a flexible image transmission system and is distinguished by the fact that the flexible image transmission system ends in an imaging device (2), which is arranged between the objective lens (10) and the object plane of the operation microscope (1) and can be removed from the beam path.

14 Claims, 3 Drawing Sheets

ENDOMICROSCOPE SYSTEM

FIELD OF THE INVENTION

The invention relates to an endomicroscope system, comprising an operation microscope and a flexible image transmission system.

BACKGROUND OF THE INVENTION

Operation microscopes are used in a variety of medical disciplines in order to perform microsurgical work on fine structures. Thus, there are specific operation microscopes for ophthalmology, neurosurgery, dental medicine and numerous other fields.

In many cases, however, the direct view through the microscope is limited. Thus, in ophthalmology, hemorrhages may obstruct or prevent the view of the retina through the vitreous humor. In neurosurgery, in the event of access through the brain to a tumor, there is a desire to observe said tumor from the side or underside, in order to identify concrescence with blood vessels or nerves early on. In dental medicine, at the present time only few operations are actually performed with an operation microscope, since the rimose topology of the jaws allows only few areas of teeth or gum to be identified. It is important, furthermore, that a stereoscopic image is generated in order that the surgeon can estimate the depth of the operation field.

Microscopes are known which allow a particular mobility by virtue of a cardanic suspension and are used in neurosurgery. Such a microscope is described in DE-A-43 11 467. The problem of looking beside or behind a structure cannot, however, be solved by this microscope either. Moreover, this microscope cannot significantly improve the occlusion in dental medicine, since the viewing direction is limited from the outset.

The patent specifications DE-C-41 16 810, DE-C-42 25 507 and U.S. Pat. No. 5,496,261 in each case describe combinations of endoscopes with operation miscroscopes and operation microscope-like views on endoscopes. Although this results in stereoscopic vision through an endoscope and, if appropriate, the endoscope can be pivoted away in order to use the operation microscope on its own, these combinations of endoscopes and operation microscopes are not suitable for the purpose of use described above. The rigid coupling of microscope and endoscope does not allow free mobility of the endoscope tip, with the result that occlusions continue to occur. Moreover, it is possible for relative movements to occur between the patient, who is in each case only locally anaesthetized in ophthalmology and dental medicine, and the endoscope, as a result of which the rigid arrangement may not only lose the image but become a hazard for the patient.

Admittedly, DE-C-42 25 507 describes the use of flexible endoscopes enabling the last-mentioned disadvantage to be avoided. However, the citations reveal that the endoscope generates an image at a location corresponding to the location of the object if the microscope is used as a customary microscope. In this case, the endoscope with the imaging device by which the image to be observed is generated is situated on that side of the object plane which is remote from the objective lens. If, therefore, one wishes to observe the object previously observed through the endoscope directly with the microscope, not only does the endoscope have to be removed, but also the microscope has to be moved closer to the object and focused This means a considerable effect in respect of adjustment.

SUMMARY OF THE INVENTION

The object of the invention consists in providing an endomicroscope system which is adjustable in such a way that the object can be sharply imaged without readjustments of the operation microscope on the one hand with a flexible image transmission system and on the other hand after the removal of the same without this image transmission system.

The solution according to the invention consists in the fact that the flexible image transmission system ends in an imaging device, which is arranged between the objective lens and the object plane of the operation microscope and can be removed from the beam path.

Thus, unlike in the case of the prior art, the imaging system is not arranged on the other side of the object plane, as seen from the objective lens, but rather between the object plane and the objective lens. After the removal of the image transmission system, the object plane is then situated clearly below the operation microscope. In this case, the arrangement can readily be chosen such that the object plane of he microscope coincides with the object plane of the endomicroscope system, which comprises the operation microscope and the flexible image transmission system. Thus, a sharp image is obtained both by means of the flexible image transmission system and without adjustment of the operation microscope without the same, if the image transmission system is removed from the beam path.

The imaging device is expediently fitted pivotably on the operation microscope.

In this case, the endomicroscope system of the invention is expediently designed in such a way that the imaging device contains optical elements, which image images in or near the imaging device into one or both beam paths of the operation microscope in such a way that a parallel pencil of rays is produced behind the objective lens of said microscope. This pencil of rays can then be observed through the eyepiece as in the case of a normal microscope.

It is expediently provided that the optical elements are converging lens arrangements whose principal planes are at a distance from the images which is less than the focal length of the optical elements.

An advantageous embodiment provides for the image transmission system to have two separate transmission channels whose images, in the imaging device, are radiated separately into the two beam paths of the operation microscope.

If the spacing of the ends of the transmission channels on the side facing the object is variable (stereo variator), then the stereoscopic effect can be magnified or diminished. In an advantageous embodiment, the image transmission system comprises one or more flexible endoscopes, in particular oriented bundles of fibers are used in this case. On the object side, the image is imaged onto one end of the bundle of fibers. The identical image at the other end of the bundle of fibers is then guided via the imaging device into the microscope beam path.

In another embodiment, the image transmission system comprises one or more video endoscopes. CCD chips are known for this purpose which have a diameter of just ¼ inch (approximately 6 mm), with the result that they can be fitted on the tip of the image transmission system (endoscope) introduced into the body. Monitors are then situated at the other end of the image transmission system, the image of which monitors is guided into the microscope beam path by the imaging device in exactly the same way as the image of the oriented bundle of fibers in the first embodiment.

The image recording system on the side facing the object expediently has an image sensor, in which there is fitted an imaging optical system separated from the object by a window. In this case, it is particularly expedient if a supply line through which compressed air from an external source can be conducted is integrated in the image sensor, and if an outlet opening is present for the compressed air and is configured in such a way that the compressed air can flow across the window. The window can be cleaned in this way.

As was mentioned in the introduction, the imaging device should be able to be removed from the beam path. This can be done on the one hand by said imaging device being fitted pivotably on the operation microscope. However, it is also possible for the image transmission system to be designed as a module that can be mounted and demounted.

According to the invention, it may be provided that the light for illuminating the observation field is guided by the flexible image transmission system. Thus, the image transmission system is used not only for observing the observation field but also for illumination. It is not necessary, therefore, to use a separate optical waveguide or the like, with the result that the elements to be introduced into the body are not enlarged by the illumination arrangement.

An advantageous embodiment provides a separate light source for the flexible image transmission system, which can be removed from the microscope together with the image transmission system, thereby enabling normal observation of the observation field with the microscope. Another advantageous embodiment provides for the light of the microscope illumination that is present in any case to be used, with the result that an additional light source can be dispensed with. The light is expediently coupled into the imaging device fitted on the pivotable operation microscope, with the result that here it is not necessary to establish or disconnect any further connections for the illumination when the flexible image transmission system is connected to the microscope or detached from the same.

The arrangement according to the invention can essentially be described by the combination of an operation microscope with a flexible image transmission system which is used like a flexible endoscope but whose image is reflected into the operation microscope. What is essential in this case is that the reflection is effected by means of an optical system close below the objective lens of the operation microscope. As a result of the proximity to the object, the working distance is preserved and the object is seen sharply through the operation microscope if the reflection apparatus is pivoted away. Moreover, when the reflection apparatus is pivoted into place, the visual path to the object is concealed, so that only the endoscopic image is seen.

BRIEF DESCRIPTION OF THE DRAWINGS

The invention is described below using advantageous embodiments with reference to the accompanying drawings, in which.

DETAILED DESCRIPTION OF A PREFERRED EMBODIMENT

Figure 1:
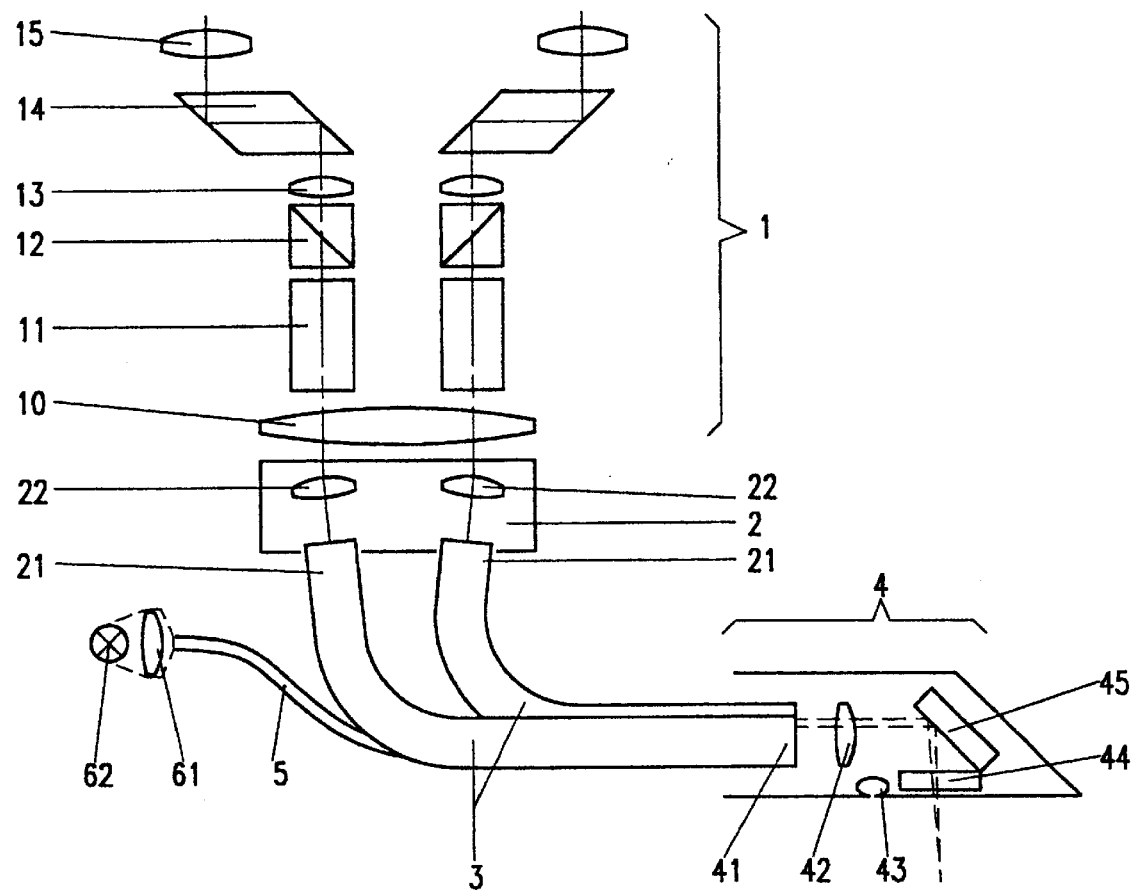
FIG. 1 shows a schematic view of a first embodiment.

FIG. 1 shows an operation microscope 1 comprising an objective lens 10, a zoom system 11, beam splitters 12 for coupling out part of the light coming from the object to cameras or co-observers and an optical imaging arrangement 13, above which an inverting system 14 and eye pieces 15 are situated. There is a parallel optical beam path between the objective lens 10 and the optical imaging arrangement 13.

Situated below the objective lens 10 of the operation microscope 1 is an imaging device 2 which can be pivoted into place and contains optical elements 22 which image the light emerging from optical waveguide ends 21 in such a way that a parallel beam path is produced in connection with the objective lens 10. For this purpose, the optical elements 22 comprise converging lenses or are lens systems which act as converging lenses and whose distance, calculated from the principal plane, from the optical waveguide ends 21 is less than their focal length.

The optical waveguides 3, one each for the left and right visual channel, comprise oriented bundles of fibers. An imaging of an object onto the distal end 41 of an optical waveguide 3 is forwarded and generates a corresponding image at the proximal end 21, which can then ultimately be seen sharply through the eyepieces of the operation microscope 1.

At the distal end, the optical waveguides 3 end in the moveable image sensor 4. The latter preferably comprises a casing with a window 44, through which the light from an object is imaged onto the optical waveguide ends 41 via a mirror 45 by means of the optical arrangement 42. An exit opening for compressed air is provided near the window 44, in order to enable cleaning of aerosols. The supply line from a compressed air generating unit to the exit opening 43 is not shown in the example for the sake of clarity.

Illumination light is directed to the operation field via a further optical waveguide 5, which may comprise an unoriented bundle of fibers. The illumination light is either generated in a separate light source 62 and coupled into the optical waveguide 5 via an optical illumination arrangement 61 or is taken from the illumination light of the operation microscope (not shown). In the latter case, the optical waveguide 5 and the optical coupling-in arrangement 61 are preferably integrated in the reflection apparatus 2, so that after they have been pivoted away, the operation microscope is functional without limitation.

The mobility of the optical waveguides 3 is of great importance This enables the surgeon, when working with the moveable image sensor 4, to hold the latter in his hand and simultaneously support it on the body of the patient. As a result relatively small movements of the patient do not lead to relative movements between the object and the image sensor 4.

Figure 2:
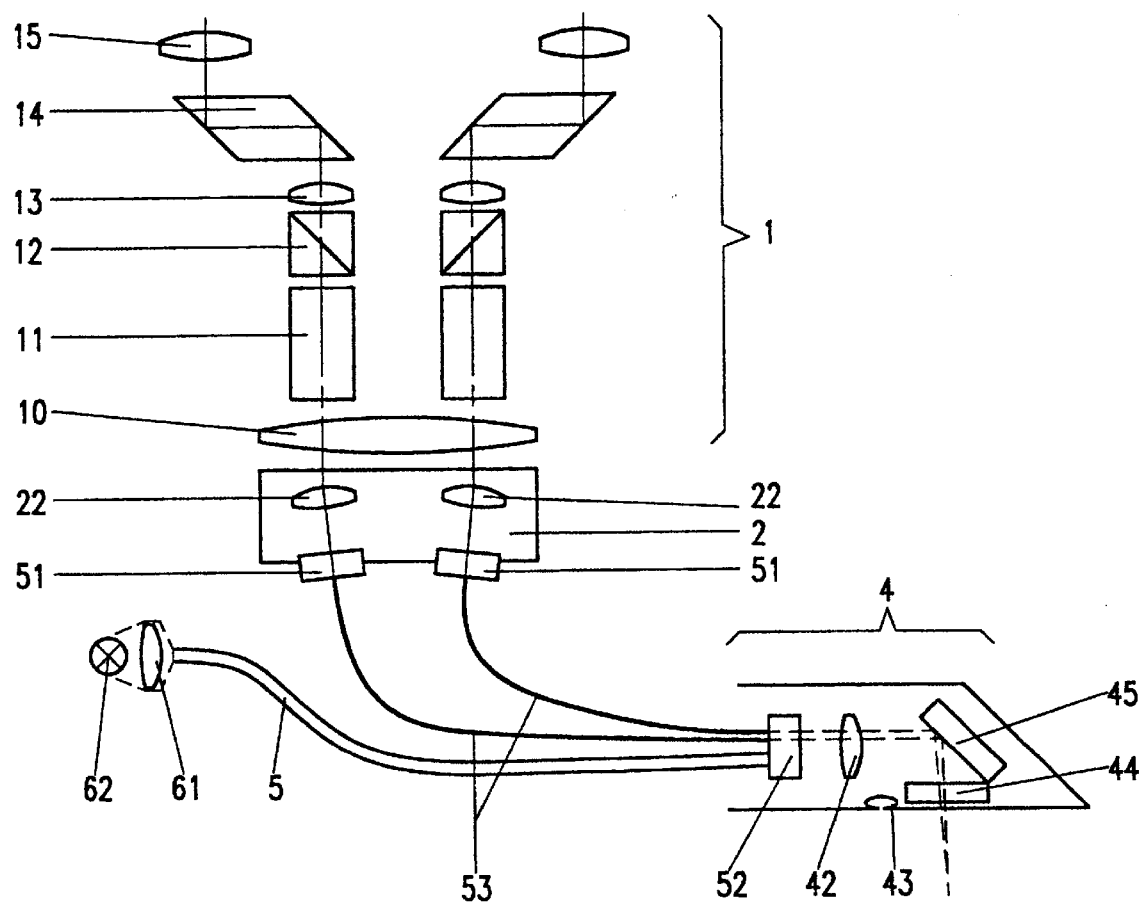
FIG. 2 shows a schematic view of a second embodiment of the invention.

In the embodiment of FIG. 2, video cameras are provided instead of the oriented bundles of fibers. On CCD chips 52, a respective image is generated with the same optical imaging device 42, 44, 45 as in the embodiment of FIG. 1, which image is then transmitted with the aid of lines 53 to monitors 51, whose images are then guided into the microscope beam path as in the embodiment of FIG. 1. The corresponding small monitors are known from the viewfinders for video cameras. The light can be supplied to the object again by means of a small light source in the image sensor 4 or an optical waveguide 5 which receives the light from an external light source or, in the pivoted-in state, from the illumination light of the microscope.

Figure 3:
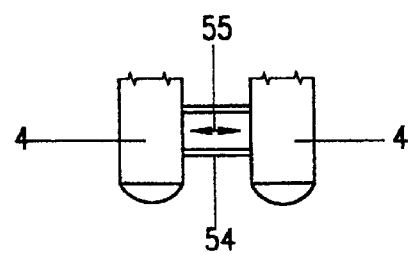
FIG. 3 schematically shows a device for altering the spacing of the transmission channels.

Depending on the task, the image sensor 4 may be provided with an apparatus which varies the spacing of two separate image sensors 4, as is indicated by guides 54 and the double arrow 55 in FIG. 3, or the spacing of the optical waveguide ends 41 or of the video CCD chips 52 in each case with the associated optical arrangement 42. As a result, a stereo variator is produced, which is particularly advantageous if sometimes narrow channels are intended to be observed even with partial dispensation with the stereoscopic effect, which, however, is intended to be maximized in the case of the surface observations.

Likewise, the image sensor 4 can be mounted on medical instruments, for example on a dental mirror when used in dental surgery. Finally, the entire flexible image transmission system may be embodied as an independent module which can be acquired separately from the operation microscope and e.g. be mounted on an existing operation microscope and removed again as required.

Figure 4:
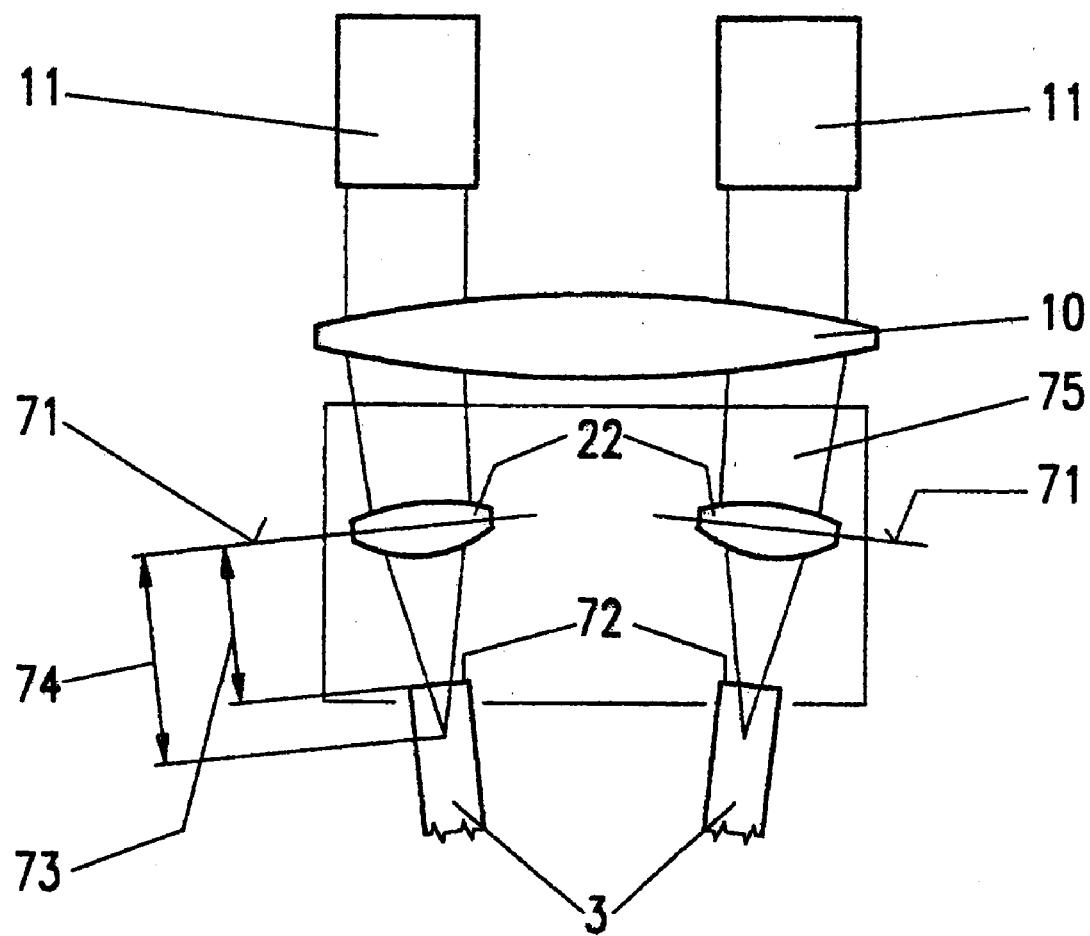
FIG. 4 shows a detail illustration of the optical imaging.

FIG. 4 shows the optical imaging in detail. In this embodiment, the optical waveguides 3 are oriented bundles of fibers which therefore exhibit the image at their end surface 72. In this case, the imaging by the lenses 22 is such that the principal planes 71 are at a distance 73 from the image surface 72 which is less than the focal length 74, with the result that the light beams 75 imaged by the lenses 22 leave the lens 22 slightly diverential as a result the light falling onto the front lens 10 is matched to the case where the imaging device 2 is not present. One thus has the possibility of working with or without the imaging device 2, without adjustment being necessary in between times.

What is claimed is:

1. An endomicroscope system, comprising an operation microscope and a flexible image transmission system, wherein the flexible image transmission system ends in an imaging device (2), which is arranged between the objective lens (10) and the object plane of the operation microscope (1) and can be removed from the beam path.

2. The endomicroscope system as claimed in claim 1, wherein the imaging device is fitted pivotably on the operation microscope.

3. The endomicroscope system as claimed in claim 1, wherein the imaging device (2) contains optical elements, which image images in or near the imaging device into one or both beam paths of the operation microscope in such a way that a parallel pencil of rays is produced behind the objective lens.

4. The endomicroscope system as claimed in claim 3, wherein the optical elements are converging lens arrangements whose principal planes are at a distance from the images which is less than that of the optical elements.

5. The endomicroscope system as claimed in claim 1, wherein the image transmission system has two separate transmission channels whose images, in the imaging device, are radiated separately into the two beam paths of the operation microscope.

6. The endomicroscope system as claimed in claim 5, wherein the spacing of the ends of the transmission channels on the side facing the object is variable (stereo variator).

7. The endomicroscope system as claimed in claim 1, wherein the image transmission system comprises one or more flexible endoscopes.

8. The endomicroscope system as claimed in claim 1, wherein the image transmission system comprises one or more video endoscopes, each comprising a video camera, a signal transmission unit and a monitor.

9. The endomicroscope system as claimed in claim 1, including an image recording system on the side of the flexible image transmission system facing the object containing an image sensor, in which there is fitted an imaging optical system, separated from the object by a window.

10. The endomicroscope system as claimed in claim 9, wherein a supply line through which compressed air from an external source can be conducted is integrated in the image sensor, and wherein an outlet opening is present for the compressed air and is configured in such a way that the compressed air flows across the window.

11. The endomicroscope system as claimed in claim 1, wherein the image transmission system is designed as a module that can be mounted and demounted.

12. The endomicroscope system as claimed in claim 1, wherein light for illuminating the observation field is guided by the flexible image transmission system.

13. The endomicroscope system as claimed in claim 12, further comprising a separate light source for the flexible image transmission system.

14. The endomicroscope system as claimed in claim 12, wherein a light source associated with the operation microscope provides the light for illuminating.

* * * * *

UNITED STATES PATENT AND TRADEMARK OFFICE
CERTIFICATE OF CORRECTION

PATENT NO. : 6,309,348 B1
DATED : October 30, 2001
INVENTOR(S) : Schmidt et al.

It is certified that error appears in the above-identified patent and that said Letters Patent is hereby corrected as shown below:

Column 5,
Lines 30-32, should read "imaging device, which is arranged between an objective lens and an object plane of the operation microscope and which is removable from a beam path of the operation microscope."

Line 37, after device delete "(2)".

Signed and Sealed this

First Day of October, 2002

Attest:

JAMES E. ROGAN
Attesting Officer
Director of the United States Patent and Trademark Office